United States Patent [19]

Tacker, Jr. et al.

[11] Patent Number: 4,548,203
[45] Date of Patent: Oct. 22, 1985

[54] SEQUENTIAL-PULSE, MULTIPLE PATHWAY DEFIBRILLATION METHOD

[75] Inventors: Willis A. Tacker, Jr.; Joe D. Bourland; Charles F. Babbs; Leslie A. Geddes, all of West Lafayette, Ind.

[73] Assignee: Purdue Research Foundation, West Lafayette, Ind.

[21] Appl. No.: 624,269

[22] Filed: Jun. 25, 1984

Related U.S. Application Data

[63] Continuation-in-part of Ser. No. 383,781, Jun. 1, 1982, abandoned.

[51] Int. Cl.$^4$ ............................................. A61N 1/36
[52] U.S. Cl. ................................. 128/419 D; 128/784
[58] Field of Search ...................... 128/419 D, 420 A

[56] References Cited

U.S. PATENT DOCUMENTS

| | | | |
|---|---|---|---|
| 3,211,154 | 10/1965 | Becker et al. | 128/419 D |
| 3,605,754 | 9/1971 | Jarus et al. | 128/419 D |
| 3,895,639 | 7/1975 | Rodler | 128/420 A |
| 3,937,226 | 2/1976 | Funke | 128/419 D |
| 4,023,574 | 5/1977 | Nemec | 128/420 |
| 4,030,509 | 6/1977 | Heilman et al. | 128/419 D |
| 4,088,140 | 5/1978 | Rockland et al. | 128/419 D |

FOREIGN PATENT DOCUMENTS

| | | | |
|---|---|---|---|
| 1109280 | 6/1961 | Fed. Rep. of Germany . | |
| 2853253 | 6/1980 | Fed. Rep. of Germany | 128/419 D |
| 2257312 | 8/1975 | France . | |
| 467502 | 6/1937 | United Kingdom | 128/420 A |

OTHER PUBLICATIONS

Rastelli et al, "Journal of Thoracic & Cardiovascular Surgery", vol. 55, No. 1, Jan., 1968, pp. 117–122 (especially FIGS. 2-3).

*Primary Examiner*—William E. Kamm
*Attorney, Agent, or Firm*—Barnes & Thornburg

[57] ABSTRACT

A method of controlling cardiac ventricular fibrillation and other tachyarrhythmias by delivery of two time-separated current pulses to separate pairs of electrodes spatially placed in, around, or on the heart. The technique produces a temporal and spatial summation of the delivered current, which results in a dramatic reduction in the voltage, current, and energy required for defibrillation, or cardioversion, and allows the use of a smaller implantable pulse generator. The new system achieves a more uniform distribution of current within the ventricular myocardium, thereby reducing the risk of tissue damage and increasing the margin of safety between effective shocks and myocardial depressing or damaging shocks.

6 Claims, 17 Drawing Figures

SEQUENTIAL-PULSE, MULTIPLE PATHWAY DEFIBRILLATION METHOD

This is a continuation-in-part of Ser. No. 383,781, filed June 1, 1982 now abandoned.

This invention relates to the control of cardiac ventricular tachyarrhythmias, including fibrillation, and more particularly to an improved method and means which function more effectively and at lower shock strength (voltage, current, and energy) than heretofore employed.

Ventricular fibrillation is an uncoordinated contraction and relaxation of the individual fibers of the heart which produces no blood flow and results in death unless corrective measures are applied within minutes of onset. Conventional treatment for the hospitalized patient calls for the application of an electric shock of sufficient strength voltage to depolarize most of the ventricular cells, e.g., by way of a pair of electrodes ("paddles") across the chest of the patient. For the patient outside the hospital who has been identified as a fibrillation risk, the shock can be applied to a pair of electrodes implanted in various ways around and within the heart, the shock being supplied by an implanted pulse generator in response to a command from a fibrillation or tachyarrhythmia detector.

Of the various implanted electrode systems heretofore employed, the most efficient comprises a pair of electrodes placed on opposite sides of the heart in the epicardial-pericardial space. A system such as that disclosed in our contemporaneously filed application entitled ELECTRODE SYSTEM AND METHOD FOR IMPLANTABLE DEFIBRILLATORS has numerous advantages over the prior-art systems, especially in avoiding thoracotomy or other major surgery for implantation, and also in avoiding placement of the electrodes in the blood stream or in the heart thereby minimizing the problems of fibrosis, blood clot and embolus formation, and associated risk of stroke and infarction.

Catheter-borne electrodes are currently used in the right ventricle. An electrode in the heart is currently paired with one electrode outside of the heart. In all of these applications, a single pulse of current is delivered to the electrodes to achieve defibrillation.

A fundamental limitation of all such electrode systems, however, is the current density not being uniform throughout the ventricles, with the result that some regions of the ventricles receive more current than necessary while other regions receive less. A larger total current is therefore required to achieve the "defibrillation threshold", and tissues in regions of high currents (usually those adjacent to the electrodes) are at a higher risk of sustaining damage.

In order to reduce the current density under the electrodes and at the same time to increase the volume of ventricular tissue exposed to the current, we explored the possibility of increasing the electrode size, either by using wider electrodes or by extending them a greater distance along the epicardial wall from base to apex. In each case, however, before the desired result could be attained, the edges or ends of the electrodes approached each other closely enough to provide a shorter alternate path for the current through the epicardial tissue, thereby reducing rather than increasing the current through the ventricles, and increasing the risk of myocardial damage.

We have succeeded in avoiding the problems related to current density in a relatively simple manner by sequentially delivering two current pulses to separate pairs of electrodes implanted in the epicardial-pericardial space. For example, we deliver two pulses to the ventricles, one in a lateral direction, and immediately before or afterward, another pulse in a ventral-dorsal direction. In this manner, we have achieved a temporal and spatial summation effect for the defibrillating current, resulting in a dramatic reduction in the voltage, current, and energy required to defibrillate when compared to all presently known electrode systems.

It should be noted that the directions taken by the current need not be at right angles, only that the directions be different and the current pulses be sequential. Moreover, it is not necessary to use two pairs of electrodes to deliver the two currents. Three appropriately placed electrodes (that is one common and two independent electrodes) can be used to achieve a temporal and spatial summation effect for the defibrillation current.

It is accordingly an object of the present invention to control cardiac ventricular fibrillation and other tachyarrhythmias in an improved and more effective manner.

Another object is to achieve a more uniform current density distribution throughout the heart, thereby avoiding areas of high current density.

Another object is to achieve cardiac ventricular defibrillation or cardioversion with less energy, lower voltage, and lower current.

A further object is to minimize the risk of myocardial damage in the control of ventricular fibrillation and other tachyarrhythmias.

A still further object is to minimize the size of implanted electrodes and implanted pulse generators used in the control of cardiac ventricular fibrillation and other tachyarrhythmias.

The objects of the present invention are achieved by the time-separated delivery of two current pulses to separate electrodes placed in or around the heart, for example, in the epicardial-pericardial space. The technique produces a temporal and spatial summation of the delivered current, which results in a dramatic reduction in the voltage, current, and energy required for defibrillation or cardioversion, and allows the use of a smaller implantable pulse generator. The new system achieves a more uniform distribution of current within the ventricular myocardium, thereby reducing the risk of tissue damage and increasing the margin of safety between effective shocks and myocardial depressing or damaging shocks.

Other objects of the invention and its advantages over the prior art will be apparent from the following description of the accompanying drawings which illustrate and compare the invention with the prior art, and also show preferrred embodiments exemplifying the best mode of carrying out the invention as presently perceived. In such drawings.

Figure 1:
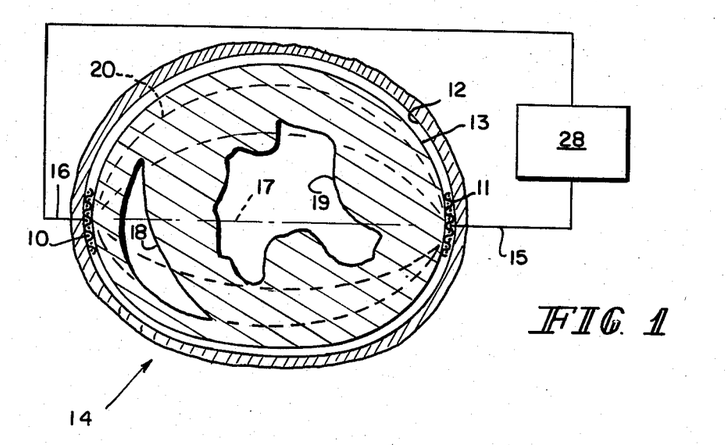
FIG. 1 is a simplified cross-section of the heart through the ventricles, looking upward, showing two laterally opposed electrodes in place on the epicardium.

FIG. 1 illustrates an important limitation of conventional electrode systems using a single pair of electrodes, even when directly opposed, in that they do not provide a uniform current density throughout the ventricles. Two laterally opposed electrodes 10 and 11 implanted between the pericardial sac 12 and the epicardium 13 of the heart 14 are attached by way of leads 15 and 16 to a control device and pulse generator 28 of known design, such as, for example, any one disclosed in U.S. Pat. Nos. 4,291,699; 4,184,493; or 4,202,340. When a pulse is applied to leads 15 and 16, the maximum current density lies mainly in the line 17 between the electrodes, passing through the tissues of the right ventricle 18 and the left ventricle 19, decreasing to a minimum near the heart wall 13 at line 20. Thus, relatively little current flows through the dorsal and ventral portions of the left ventricular tissue, and as a result a higher voltage and higher overall current density are required to achieve defibrillation or cardioversion.

Figure 2:
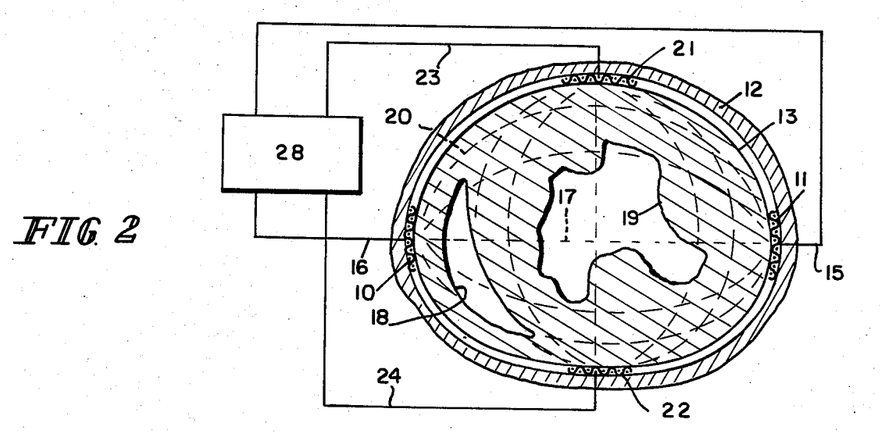
FIG. 2 is similar to FIG. 1, but with addition of two ventrally-dorsally opposed electrodes, the adjacent electrodes being placed essentially orthogonal to each other.
Figure 2A:
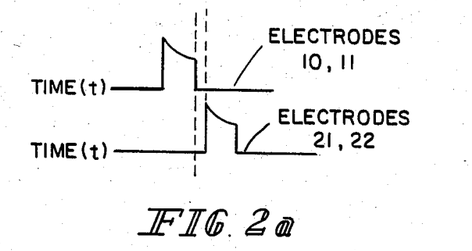
FIG. 2a is a representation of two current pulses applied to spatial electrodes, such as those in FIG. 2, showing the temporal relationship of the pulses.

In FIG. 2, a second pair of electrodes 21 and 22, placed dorsally and ventrally, are added to the arrangement of FIG. 1, with leads 23 and 24 connected to a pulse generator and controller (not shown) arranged to supply pulses, as shown in FIG. 2a, in sequence to the lateral pair of electrodes 10, 11 and to the dorsal-ventral pair 21, 22. The presence of the second pair of electrodes does not significantly alter the current distribution from the first pair, so long as the electrodes are relatively small with respect to the epicardial circumference, and so long as the two pairs of electrodes are isolated from each other during current flow. For this purpose, the distance between the adjacent edges of adjacent electrodes should not be smaller than the shorter of the distances between electrode pairs. As shown in FIG. 2, the current in the second pulse concentrates in the areas of low current density during the first pulse, with the result that the ventricular tissues are much more effectively treated, in particular the critically important left ventricle. Thus, the use of two pairs of electrodes implanted in spaced relationship permits the use of smaller electrodes, lower voltage and current, and lower total energy, which can be delivered by a smaller pulse generator, with less hazard of damage to the tissues adjacent the electrodes. For these reasons, the invention is safer and more effective than the prior art.

In the embodiment illustrated in FIG. 2, our invention will employ two sets of opposed electrodes, one pair disposed laterally upon the epicardium and the other pair disposed ventrally-dorsally, each electrode being orthogonal to the adjacent electrodes. In principle, three or more electrodes can be used, if desired, spaced more or less evenly around the epicardium and pulsed sequentially, subject only to the limitation that they must not be so close together as to divert the current flow away from the ventricular tissues. In fact, some electrodes can be inside the heart and others can be outside the heart. (See, for example, the arrangement shown in FIG. 3a.) For the typical fibrillation or tachycardia patient, however, we do not look upon such additional electrodes as either necessary or desirable, considering the additional surgery involved in installing them.

It is important to our invention to use more than two electrodes in order that the sequential pulses traverse different pathways through the heart. This is the spatial aspect of our invention.

Figure 3:
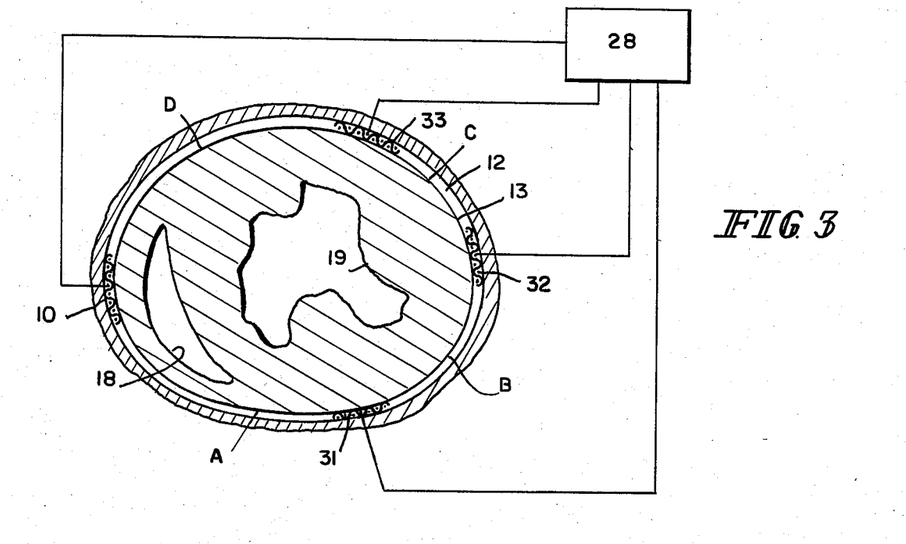
FIG. 3 is similar to FIG. 1, but with multiple left-ventricle electrodes implanted.

The location of the electrodes need not be orthogonal, nor necessarily outside the heart, but may vary somewhat, so long as the desired current flow through the left ventricular tissue is achieved. (See FIG. 3a.) Indeed, because of the disparity in size between the ventricles (the left ventricle being much larger), an advantageous alternative arrangement is to install multiple left ventricular electrodes as shown in FIG. 3 with a single right ventricular electrode and to pulse each of the left ventricular electrodes in sequence, paired with the right ventricular electrode. Thus, in FIG. 3, the epicardium adjacent the left ventricle is divided into three equal segments represented by AB, BC, and CD, and an electrode 31, 32, 33 is implanted in the pericardial space at the middle of each segment. All of the electrodes are connected to a pulse generator and controller (not shown), which sequentially pairs electrodes 31, 32, and 33 with electrode 10 and delivers a pulse. In this way, maximum depolarization of the left ventricular tissues is achieved. With this arrangement, the only limit upon the number of left ventricular electrodes that may be used is the surgical trauma involved in installing them.

Figure 3A:
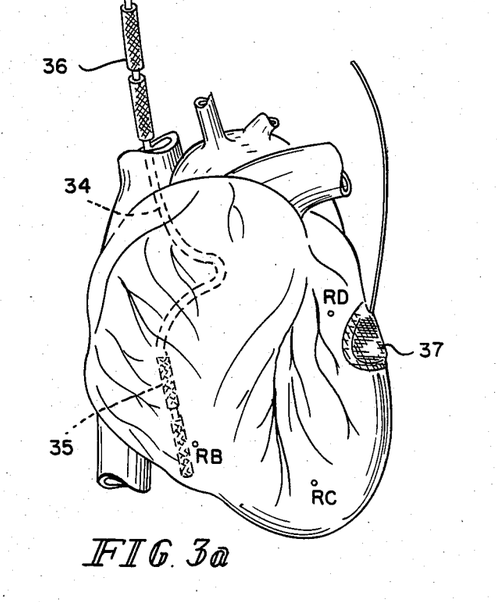
FIG. 3a is a plan view of the heart showing three spatial electrodes, one inside the heart and two outside the heart.
Figure 3B:
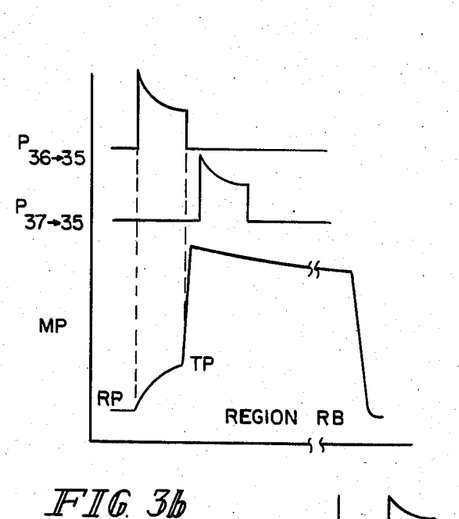
FIG. 3b is a graphical representation of heart membrane potential in region RB of the heart shown in FIG. 3a employing the temporal and spatial summation method of the present invention.
Figure 3C:
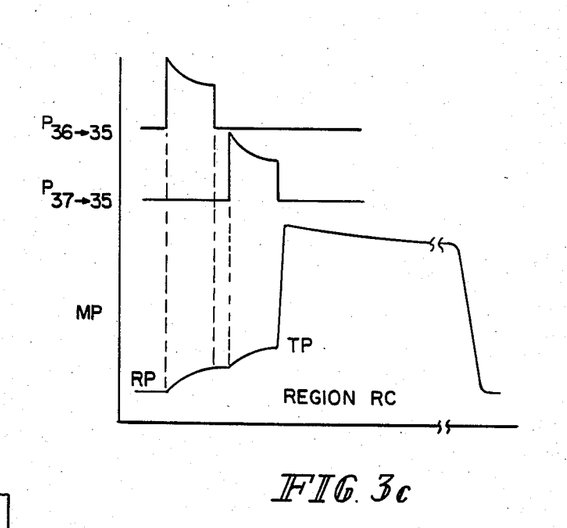
FIG. 3c is a graphical representation of heart membrane potential in region RC of the heart shown in FIG. 3a employing the temporal and spatial summation method of the present invention.
Figure 3D:
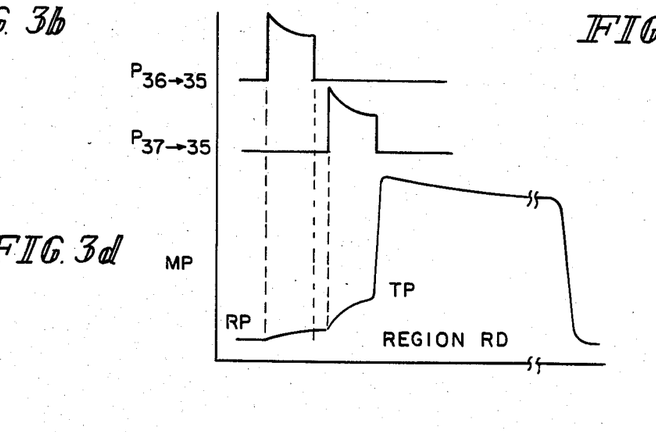
FIG. 3d is a graphical representation of heart membrane potential in region RD of the heart shown in FIG. 3a employing the temporal and spatial summation method of the present invention.

Another alternative arrangement is to use a catheter 34 carrying or including electrodes 35 and 36 as shown in FIG. 3a. One of the catheter-borne electrodes 35 is installed in the right ventricle with the other catheter-borne electrode 36 outside the heart. A third electrode 37 is installed on the left ventricle of the heart. Each of the electrodes 36, 37 is pulsed in sequence, as shown in FIG. 2a, and each is paired with the electrode 35. As in each of the embodiments discussed above (FIGS. 2 and 3), the heart may be divided into regions related to the location of the electrodes 35, 36, and 37. For example, a region RB may be selected in proximity to electrode 35, region RC may be selected somewhere between electrodes 35 and 37, and region RD may be selected in proximity to electrode 37. As will be explained later, FIGS. 3b, 3c, and 3d are graphical representations of the heart membrane potential in each of the regions RB, RC, and RD, respectively, where the temporal and spatial summation method of applying current pulses is employed according to our invention.

In carrying out the process of ventricular defibrillation or cardioversion according to the present invention, it is important to pulse the electrode pairs in sequence, with at least some time (temporal) separation between the pulses. This time separation is shown in FIGS. 2a, 3b, 3c, and 3d. On the other hand, the time of separation should be limited, since we have observed that the threshold current for defibrillation increases with separation time, above about 2 milliseconds. As a general rule, we find that a separation period of about 0.1 millisecond to about 2 milliseconds is satisfactory, and we prefer about 0.5 millisecond. This is the temporal aspect of our invention.

For use in our invention, the truncated-exponential waveform suggested by Schuder et al, *Trans. Am. Soc. Artif. Organs*, 15, 207–212, 1970, is the most practical type of pulse. (See FIG. 2a.) In order to create the smallest pulse generator for implantation, it was necessary to determine the relationship between the capacitance of the energy-storage capacitor and the voltage to which it must be charged in order to deliver the minimum sufficient current to effect defibrillation. For this purpose, we conducted a study to determine the dependence of ventricular defibrillation threshold on the duration and tilt of the truncated-exponential waveform ("tilt" being defined as the percent decrease in current during the defibrillation pulse; e.g., if, at the end of the pulse, the defibrillating current has fallen to one-third its initial value, then the tilt is 67%). We found (1) that there exists a "strength-duration" curve for defibrillation, and (2) two waveforms of the same duration are equally effective if they have the same average current. (See FIG. 2a.) The latter we have called the "Average Current Law" for defibrillation (Bourland et al, Medical Instrumentation 12:42–45, 1978).

Generally, the relation between capacitance and voltage across the elements in a system in the absence of an external source of energy can be expressed by Kirchhoff's current law as:

$$C\frac{dV}{dt} + \frac{1}{R}V = 0$$

where
C is the capacitance of the system;
V is the voltage across the system;
R is the impedance of the system;
1/R is the admittance of the system;
dV/dt is the rate of change in the voltage V with respect to time.

It is also known that voltage V of the system at a particular time t can be expressed as follows:

$$V = V_o e^{-t/RC}$$

where
$V_o$ is the initial voltage of the system;
e is a constant approximately equal to 2.71828;
t is the displacement in time from the initial voltage.

The current, I, that flows in the defibrillating circuit also decreases exponentially with time (t) and is given by:

$$I = \frac{V_o}{R} e^{-t/RC}$$

Animal studies have shown (Bourland et al, Medical Instrumentation 12:42–45, 1978) that the current required to defibrillate is given by:

$$I = K_1 + K_2/d$$

where
d is the duration of a rectangular pulse used for defibrillation
$K_1$ and $K_2$ are constants which depend on the electrode system, patient species, and heart size.

The average current for a truncated-expontial waveform with duration, d, is given by:

$$I = \frac{V_o}{Rd} \int_o^d e^{-t/RC} dt$$

$$I = -\frac{RC\,V_o}{Rd} [e^{-t/RC}]_o^d$$

$$I = -\frac{CV_o}{d} (e^{-d/RC} - 1)$$

$$I = \frac{CV_o}{d} (1 - e^{-d/RC})$$

Combining these relationships and invoking the average current law for defibrillation, the voltage, $V_o$, to which the defibrillator must be charged, is given by:

$$K_1 + K_2/d = \frac{CV_o}{d} (1 - e^{-d/RC})$$

$$V_o = \frac{K_1 d + K_2}{C(1 - e^{-d/RC})}$$

Thus, the voltage $V_o$ to which the energy storage capacitor must be charged, if the generator losses are negligible, can be expressed as the following equation:

$$V_o = \frac{K_1 d + K_2}{C(1 - e^{-d/RC})}$$

The above equation permits selecting the smallest possible capacitor for use in an implantable defibrillator.

For use in our invention, pulses of truncated-exponential waveform of about 1 millisecond to about 5 milliseconds, applied to each electrode pair, are suitable, preferably around 2.5 milliseconds, with appropriate separation between pulses as described above. Depending upon the electrode system employed, the delivered voltage will range between about 80 volts and about 450 volts. In preferred forms of our invention, the voltage is selectable between 80 and 450 volts in order that the appropriate and effective dose for defibrillation can be used. Of course, lower voltages could be used for cardioversion. The threshold defibrillation current ranges from about 5 amperes to about 10 amperes. The delivered energy for the preferred form of our invention ranges from one-fourth to three-fourths less than the threshold energy required for defibrillation in other systems.

Graphical representations of the uniform current density distribution achieved throughout the heart using our spatial and temporal sequential pulsing method are shown in FIGS. 3b, 3c, and 3d. Using the electrode arrangement shown in FIG. 3a, sequential pulses such as those shown in FIG. 2a were applied between electrodes 36 and 35 and electrodes 37 and 35. In FIGS. 3b, 3c, and 3d, these pulses are identified as P36→35 and P37→35. Regions of the heart (see FIG. 3a) were selected and identified for measurement of heart membrane potential (MP). Region RB was selected in proximity to electrode 35, region RC was selected between electrodes 35 and 37, and region RD was selected in proximity to electrode 37. The heart membrane potential was measured in regions RB (FIG. 3b), RC (FIG. 3c), and RD (FIG. 3d) of the heart, both during and after application of the time-separated pulses P36→35 and P37→35. In each region, prior to the application of the pulses P36→35 and 37→35, the heart membrane was at resting potential (RP). As shown in FIG. 3b, after application of pulse P36→37, region RB achieved the threshold potential (TP) for defibrillation, but regions RC and RD did not achieve the threshold potential (TP). As shown in FIGS. 3c and 3d, after application of the second pulse P37→35, regions RC and RD both achieved the threshold potential (TP) for defibrillation. Thus, by applying time separated (temporal) pulses P36→35 and P37→35 in sequence to spaced-apart electrodes 35, 36, 37, a threshold potential (TP) is achieved not only in proximity to the electrodes but also in between the electrodes, thereby resulting in uniform current density distribution throughout the heart.

The following chart is a comparison of current, voltage, and energy requirements to achieve defibrillation using different electrode arrangements and pulse applications:

| | System | Capacitance micro-f | Delivered Current amps | Delivered Voltage volts | Delivered Energy joules | Comparison percent |
|---|---|---|---|---|---|---|
| (I) | Catheter | 35 | 6.1 | 760 | 9.69 | 100 |
| (II) | Lateral | 60 | 11.4 | 720 | 17.15 | 177 |
| (III) | Dorsal-Ventral | 60 | 5.1 | 460 | 4.90 | 82 |
| (IV) | Sim. LAT | 30 | 7.8 | 370 | 3.02 | 59 |
| | D-V | 30 | 6.0 | 430 | 2.70 | |
| (V) | SPD LAT | 30 | 4.7 | 255 | 1.25 | 25 |
| | D-V | 30 | 3.6 | 305 | 1.15 | |

As a reference for comparison, a single pulse was applied to two electrodes on a catheter, for example, between electrodes 36 and 35 shown in FIG. 3a. The requirements for achieving defibrillation are shown in the horizontal column I in the chart. Next, an identical single pulse was applied to two electrodes spaced laterally, for example, electrodes 10 and 11 shown in FIG. 1. The requirementst for achieving defibrillation are shown in the horizontal column II in the chart. It will be noted that the energy required to defibrillate using a single pulse and the FIG. 1 electrode arrangement was substantially greater than the energy required using a single pulse and catheter-borne electrodes 35 and 36. Next, an identical single pulse was applied to two electrodes spaced dorsal-ventral, for example, electrodes 21 and 22 shown in FIG. 2. The requirements for achieving defibrillation are shown in the horizontal column III in the chart. Next, two identical pulses were applied simultaneously (sim.) to one pair of electrodes spaced laterally and one pair of electrodes spaced dorsal ventral, for example, the electrode arrangement shown in FIG. 2. The requirements for achieving defibrillation are shown in the horizontal column IV on the chart.

The horizontal column V in the chart shows the requirements for achieving defibrillation using the spatial and temporal sequential pulsing method (SPD) of our invention. Time separated (temporal) pulses, such as those shown in FIG. 2a, were applied to laterally spaced and dorsal-ventral spaced electrodes (see FIG. 2). As shown by the comparison in the chart, the method of our invention required only 25% of the energy required using catheter-borne electrodes and a single pulse. The placement of four orthogonal epicardial electrodes provided a 75% decrease in defibrillation energy through the system.

This study was then undertaken to determine the threshold when only three electrodes were used, e.g., FIG. 3a, since placement of fewer electrodes is technically desirable.

In 12 dogs (mean body weight=21.6 kg), defibrillation threshold was determined for a single-pulse system using a transvenous lead (Medtronic 6882) and was compared to the defibrillation threshold for a sequential-pulse system consisting of the transvenous lead and an additional epicardial-patch electrode, placed at the left ventricular apex (FIG. 3a). The transvenous lead contains two electrodes 35 and 36 in FIG. 3a, each having a surface area of 2.5 sq cm and the surface area of the epicardial-patch electrode 37 being 1.25 sq cm. In the single-pulse system, a 10-ms rectangular pulse of current was passed from an electrode (36) in the superior vena cava (SVC) to an electrode (35) in the right ventricle (RV); in the sequential-pulse system, a 5-ms rectangular pulse of current was passed from the SVC electrode (36) to the RV electrode (35), and after a 1-ms delay, a second 5-ms rectangular pulse was passed from the epicardial-patch electrode (37) to the RV electrode (35). Energy threshold for the single-pulse system as $14.3 \pm 3.45$ (sd$\pm$sem) joules. Threshold for the sequential pulse system was $7.99 \pm 1.6$ joules ($p < 0.05$). As substantiated by these examples, using sequential pulses can greatly reduce shock strength for automatic implantable defibrillation and hence reduce the pulse generator size.

Reduction of voltage, current, and energy required to defibrillate, reduction in pulse magnitude and duration, and improvement in the uniformity of current distribution within the ventricles, using our method, reducees the risk of myocardial damage from the defibrillator shock.

An example of our invention using two pairs of electrodes, implanted subpericardially by way of an endoscope, is illustrated in FIGS. 4–12.

Figure 4:
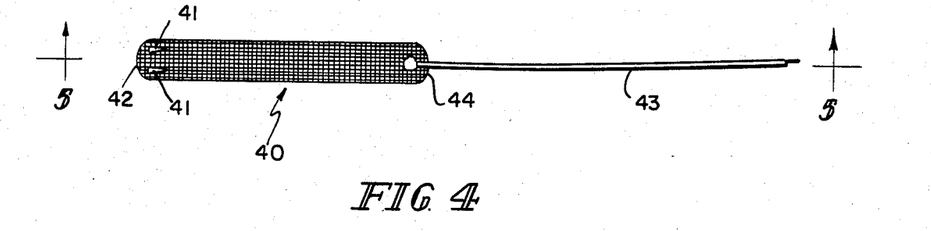
FIG. 4 is a plan view of an electrode useful in the present invention.

In FIG. 4, electrode 40 is a rectangular screen of titanium having one or more barbs 41 near one end 42 (the distal end when implanted) extending proximally, and an insulated lead wire 43 attached to the other end 44. The electrode 40 is inserted into the pericardial space with the barbs toward the pericardium, so that it becomes affixed to the pericardium by any reverse motion, such as the withdrawal of the cannula as described below.

Figure 5:
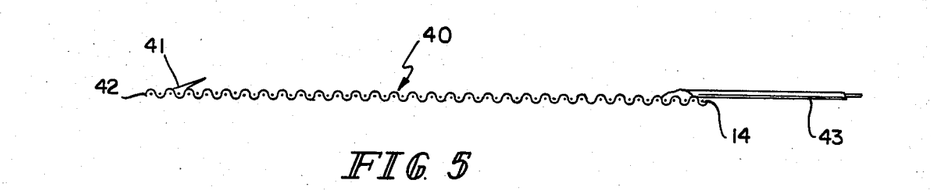
FIG. 5 is a view in cross-section of the electrode of FIG. 4 at line 5—5.

FIG. 5 illustrates the electrode 40 of FIG. 4 in cross-section at line 5—5, showing barb 41 near distal end 42 pointing proximally.

Figure 6:
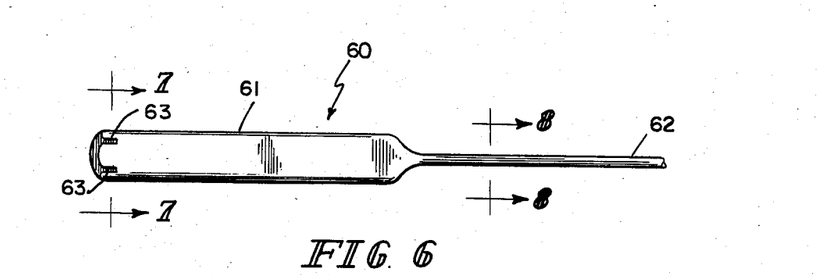
FIG. 6 is a plan view of a cannula useful in the present invention.
Figure 7:
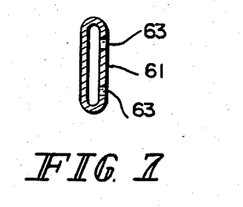
FIG. 7 and 8 are cross-sectional views of the cannula of FIG. 6 at lines 7—7 and 8—8, respectively.
Figure 8:
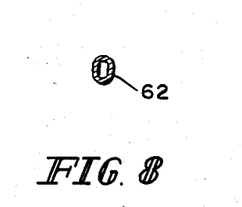

FIG. 6 illustrates a cannula 60 suitable for inserting the electrodes used in the present invention. The device is a tube, preferably made of a somewhat flexible substance such as polyethylene, flattened at its distal end 1 and optionally flattened to some extent at its proximal end 62. (See cross-sectional views at lines 7—7, FIG. 7, and 8—8, FIG. 8, respectively.) Slots 63 are provided in distal end 61 to accommodate and at least partially cover barbs 41 during insertion and to allow subsequent withdrawal of the cannula.

Figure 9:
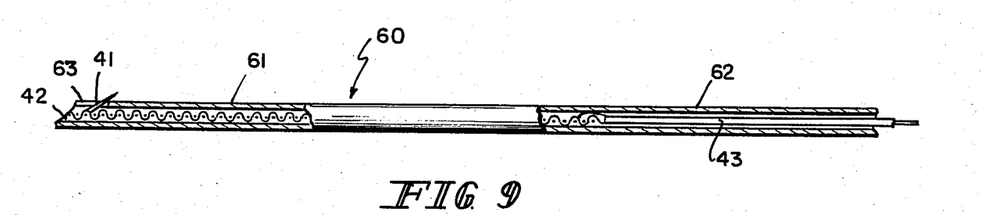
FIG. 9 is a cross-sectional view of the cannula of FIG. 6 showing the electrode of FIG. 4 in place therein.

FIG. 9 shows cannula 60 in cross-section with electrode 40 lying in position within it, the barbs 41 extending into slots 63 and lead wire 43 protruding from proximal end 62.

Figures 10, 11, 12:
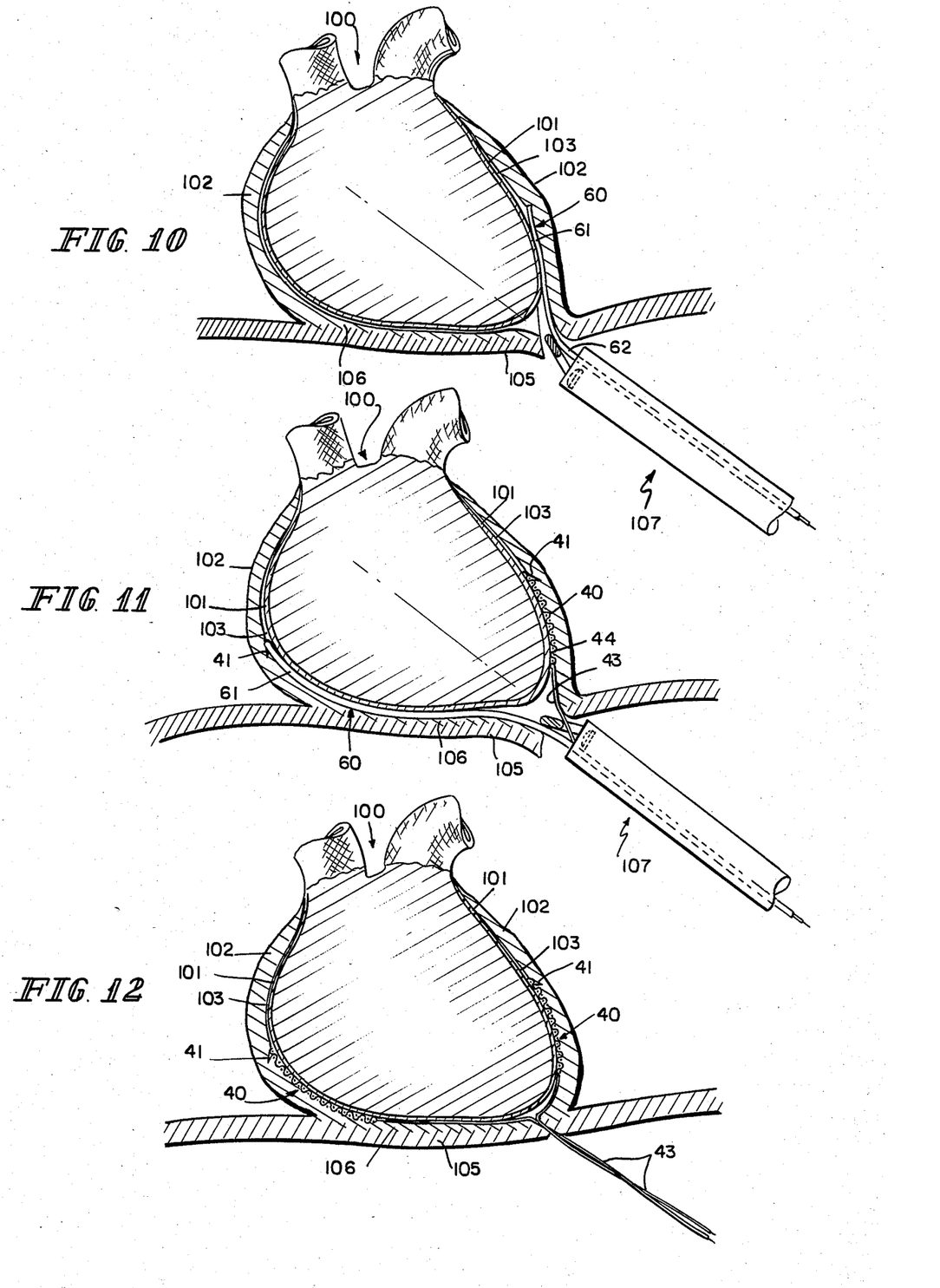
FIG. 10 is a frontal view of the human heart, partly in lateral cross-section, showing an endoscope inserted to the juncture of the pericardium and the diaphragm beneath the heart.
FIG. 11 is the same view as FIG. 10, with the cannula-electrode assembly of FIG. 9 in place in the pericardial space on the right side of the heart.
FIG. 12 is the same view as FIG. 11, with the cannula and the endoscope removed, leaving the electrode in place in the right pericardial space.

FIGS. 10, 11, and 12 illustrate one method for inserting electrodes for use in our invention.

FIG. 10 is a view of the heart 100 showing the outer surface 101 of the heart (the epicardium), the outer sac 102 enclosing the heart (the pericardium), the pericardial space 103 lying between them, the diaphragm 105 separating the thorax from the abdomen, the pericardium-diaphragm juncture 106 at which the two fuse into a single membrane, and an endoscope 107 having its distal end resting against membrane 106. The endoscope is of conventional design having two barrels, one fitted with a light and optical means for observation, and the other open for insertion of operating devices. The endoscope is inserted into the abdominal cavity through an incision in the abdominal wall and is moved upward and rested against membrane 106 at a point beneath the left central portion of the heart. A small knife is inserted through the operating barrel and an incision is made in membrane 106 of a size to admit the distal end 61 of cannula 60. The knife is withdrawn and cannula 60, with electrode 40 and lead wire 43 in place, is inserted through the operating barrel and pushed forward, curving to the right and upward into the pericardial space on the right side of the heart as shown in FIG. 11. In this position, barbs 41 hook into the wall of the pericardium and retain electrode 40 in place when cannual 60 is withdrawn, as shown in FIG. 12.

A second electrode is implanted on the left side of the heart according to the same procedure, with appropriate manipulation of cannula 60 to start the motion of the cannula and electrode 40 toward the left side of the heart. In the same way, a third electrode is implanted ventrally and a fourth electrode dorsally.

Other embodiments of our invention use electrodes in the right ventricle, coronary sinus, or under the skin of the chest wall.

The pulse generator and control unit 28 are implanted in a known way under the skin, usually of the abdomen or chest, and are connected internally to the lead wires. The device is then ready to function. Sensing devices in the control unit detect the onset of fibrillation or tachycardia and apply the necessary control pulses to the implanted electrodes, thereby restoring the normal heart beat.

The spatial and temporal sequential pulsing used in our invention reduces the current required for defibrillation threshold and therefore allows electrodes of smaller size to be used safely. For example, this is an advantage in the endoscopic method for implantation, which tends to limit the electrode width, more particularly because a smaller endoscope is preferred in order to minimize surgical trauma. Thus, the electrode width is usually around 5 to 10 mm. The electrode length is limited by the need to avoid having the electrodes too close together at the cardiac base and apex, which would tend to short-circuit the electrical path. As noted above, the electrodes should preferably be no closer to each other at any point than the straight line through the heart beween the pairs of electrodes. A suitable length is from about 10% to about 25% of the circumference of the heart. Depending upon the size of the heart, this will range from about 3 cm to about 9 cm.

The spatial and temporal sequential pulsing used in our invention reduces the energy required for defibrillation and therefore allows the use of a pulse generator about one half ($\frac{1}{2}$) the size of a pulse generator used in single pulse systems.

A further advantage of our invention is improved safety resulting from the more uniform distribution of current, thereby avoiding areas of high current density which are known to injure the heart.

The high efficiency inherent in the spatial and temporal sequential pulsing technique of our invention allows a small generator implant and use of electrodes without a thoracotomy.

While we have described our invention with references to certain specific embodiments, such embodiments are set forth as illustrative only and not by way of limitation. Numerous modifications will be apparent to those skilled in the art without departing from the spirit of the invention.

What is claimed is:

1. A method for controlling ventricular fibrillation or tachycardia which comprises implanting one pair of electrode laterally and another pair of electrodes ventrally-dorsally and subjecting each of said pairs of electrodes in sequence to an electrical pulse at a voltage between about 80 and about 450 volts for a time between about 1 and about 5 milliseconds, the pulses being separated by an interval of about 0.1 millisecond to about 2 milliseconds.

2. A method for controlling ventricular fibrillation or tachycardia which comprises implanting one electrode adjacent the right ventricle and a plurality of spaced-apart electrodes adjacent to the left ventricle, and sequentially pairing and pulsing the right ventricular electrode with the left ventricular electrodes at a voltage between about 80 and about 450 volts, the pulses being separated by an interval of at least about 0.1 millisecond to about 2 milliseconds.

3. A method for controlling fibrillation or tachycardia comprising the steps of implanting at least three spaced-apart electrodes adjacent the heart, sequentially pairing the electrodes with each other, and sequentially pulsing each pair of electrodes at a voltage between about 80 and about 450 volts, each pulse having a duration of about 1 millisecond to about 5 milliseconds and the pulses being separated by a time interval of at least about 0.1 millisecond.

4. The method of claim 3 wherein the step of implanting the electrodes on the heart comprises implanting a first one of the electrodes adjacent either the right or left ventricle and implanting the remaining electrodes adjacent the other ventricle in spaced relationship to each other, and the step of sequentially pairing the electrodes comprises sequentially pairing each of the remaining electrodes with the first one of the electrodes.

5. The method of claim 3 wherein the pulses are separated by a time interval of about 0.1 milliseconds to about 2 milliseconds.

6. A method for controlling fibrillation or tachycardia comprising the steps of implanting at least three spaced-apart electrodes adjacent the heart, sequentially pairing the electrodes with each other to provide at least two current pathways through the heart, and sequentially pulsing each pair of electrodes at a voltage between about 80 and about 450 volts by applying time-separated truncated-exponential pulses with 67% tilt to each electrode pair, each pulse having a duration of about 1 millisecond to about 5 milliseconds, and the pulses being separated by a time interval of about 0.1 millisecond to about 2 milliseconds.

* * * * *